United States Patent
Schick et al.

(10) Patent No.: US 10,001,454 B2
(45) Date of Patent: Jun. 19, 2018

(54) SINGLE-USE SENSORS IN BIOREACTORS, BIOTECH PURIFICATION AND BIOPROCESSING

(71) Applicant: Parker-Hannifin Corporation, Cleveland, OH (US)

(72) Inventors: Karl G. Schick, Madison, WI (US); David Uhen, Burlington, WI (US)

(73) Assignee: Parker-Hannifin Corporation, Cleveland, OH (US)

( * ) Notice: Subject to any disclaimer, the term of this patent is extended or adjusted under 35 U.S.C. 154(b) by 309 days.

(21) Appl. No.: 14/651,133

(22) PCT Filed: Mar. 12, 2014

(86) PCT No.: PCT/US2014/024353
§ 371 (c)(1),
(2) Date: Jun. 10, 2015

(87) PCT Pub. No.: WO2014/150832
PCT Pub. Date: Sep. 25, 2014

(65) Prior Publication Data
US 2015/0323486 A1    Nov. 12, 2015

Related U.S. Application Data

(60) Provisional application No. 61/788,708, filed on Mar. 15, 2013.

(51) Int. Cl.
*G01N 27/26* (2006.01)
*G01N 27/30* (2006.01)
(Continued)

(52) U.S. Cl.
CPC ....... *G01N 27/302* (2013.01); *G01N 27/4167* (2013.01)

(58) Field of Classification Search
None
See application file for complete search history.

(56) References Cited

U.S. PATENT DOCUMENTS 5,223,117 A    6/1993   Wrighton et al.
5,296,125 A    3/1994   Glass et al.
(Continued)

FOREIGN PATENT DOCUMENTS

EP   0 520 443    8/1997
EP   1 730 509    9/2005
(Continued)

OTHER PUBLICATIONS

PCT/US2014/924353 Notification Concerning Transmittal of International Preliminary Report on Patentability (Chapter I of the PCT), dated Sep. 24, 2015.
(Continued)

*Primary Examiner* — Jill A Warden
*Assistant Examiner* — Brittany I Fisher
(74) *Attorney, Agent, or Firm* — Cook Alex Ltd.

(57) ABSTRACT

Presteralized manifolds having disposable multi-functional sensors are provided which are designed for sterile packaging and single-use approaches. These manifolds, which have disposable tubing and flexible-wall containers and are adapted to interact with other equipment which can be operated by a controller and a flow-imparting unit, provide automated and accurate delivery or purification of biotechnology fluid. The disposable sensor monitors pH, oxygen and electrical conductivity, alone or in combination, that interact with the controller or are connected to a separate user interface. Disposable sensor components and re-usable components can be dockable with each other.

22 Claims, 6 Drawing Sheets

(51) Int. Cl.
*G01N 27/416* (2006.01)
*F16K 3/00* (2006.01)
*B01L 99/00* (2010.01)

(56) References Cited

U.S. PATENT DOCUMENTS

| | | | |
|---|---|---|---|
| 6,712,963 B2* | 3/2004 | Schick | A61M 1/0209 |
| | | | 210/137 |
| 7,052,603 B2 | 5/2006 | Schick | |
| 8,197,650 B2 | 6/2012 | Kahn et al. | |
| 2002/0043487 A1* | 4/2002 | Schick | B01D 61/145 |
| | | | 210/85 |
| 2002/0095078 A1 | 7/2002 | Mannheimer et al. | |
| 2006/0118472 A1* | 6/2006 | Schick | B01D 61/18 |
| | | | 210/198.2 |
| 2008/0023328 A1 | 1/2008 | Jiang et al. | |
| 2008/0035481 A1 | 2/2008 | McCormack et al. | |
| 2009/0139298 A1 | 6/2009 | Klees et al. | |
| 2009/0256679 A1 | 10/2009 | Potyrailo et al. | |
| 2010/0185143 A1 | 7/2010 | Uhland et al. | |
| 2011/0005984 A1* | 1/2011 | Boettcher | A61M 1/3621 |
| | | | 210/137 |
| 2011/0006900 A1 | 1/2011 | Nyffeler et al. | |
| 2011/0187388 A1* | 8/2011 | Ossart | C12M 41/46 |
| | | | 324/649 |
| 2011/0278168 A1 | 11/2011 | Zhuiykov | |
| 2012/0168308 A1 | 7/2012 | McCormack et al. | |
| 2013/0029374 A1 | 1/2013 | Eberheim et al. | |

FOREIGN PATENT DOCUMENTS

| | | |
|---|---|---|
| GB | 2 450 002 | 10/2008 |
| GB | 2 451 596 | 9/2009 |

OTHER PUBLICATIONS

Communication pursuant to Article 94(3) EPC dated Jan. 8, 2016.
Sandle, et al., "Application of Sterilization by Gamma Radiation for Single-Use Disposable Technologies in the Biopharmaceutical Sector", Pharmaceutical Technology, vol. 36 . . . No, 5, May 1, 2012.
ChemEurope.com, "A Silicon Based Multisensor Chip for Monitoring of Fermentation Processes", Aug. 3, 2013.
PCT/US2014/024353, "Invitation to Pay Additional Fees And, Where Applicable, Protest Fee", dated Mar. 12, 2014.
PCT/US2014/024353 "Notification of Transmittal of the International Search Report and the Written Opinion of the International Searching Authority", dated Jan. 5, 2015.

* cited by examiner

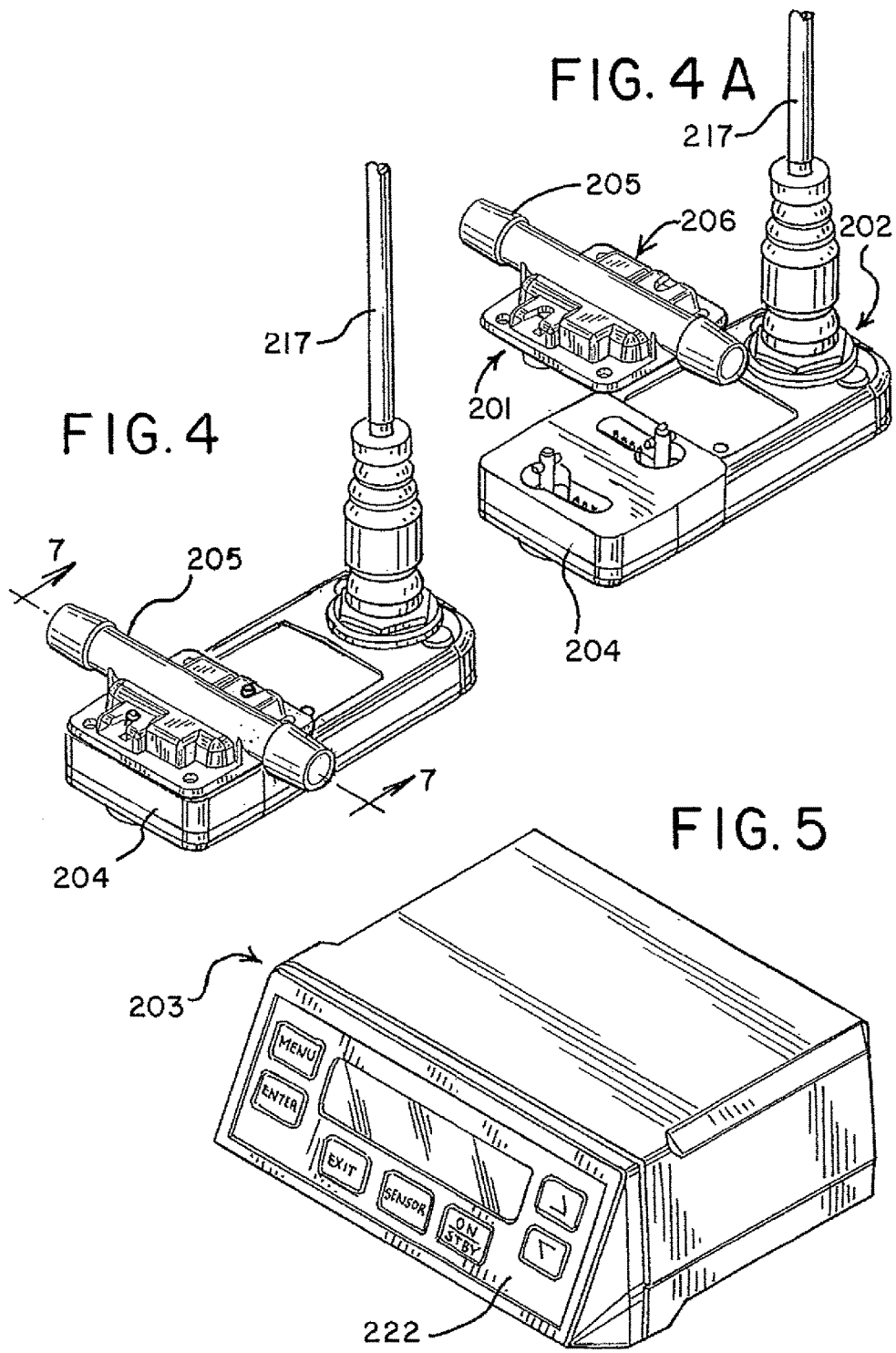

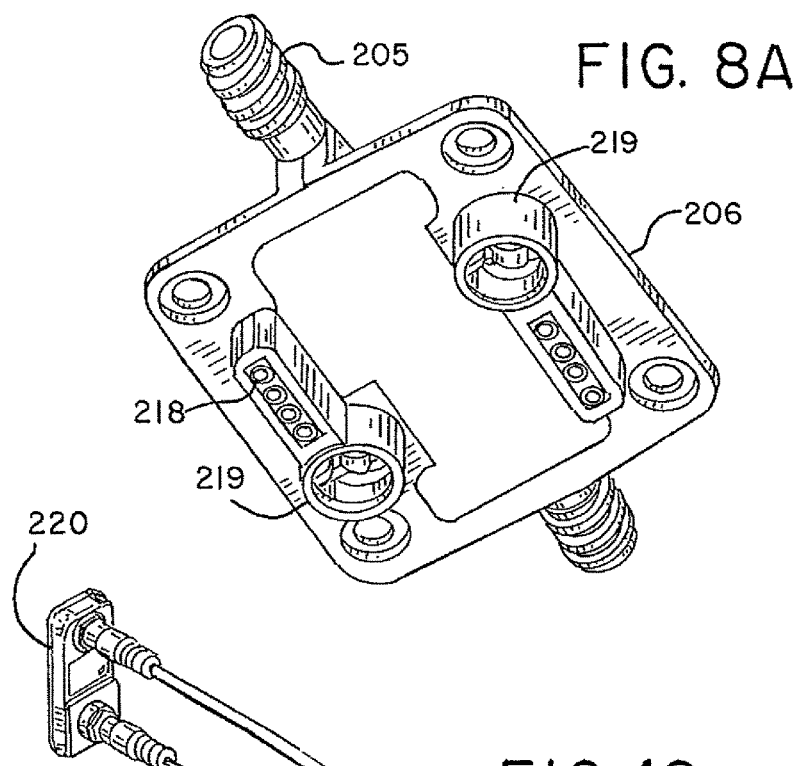
FIG. 8A
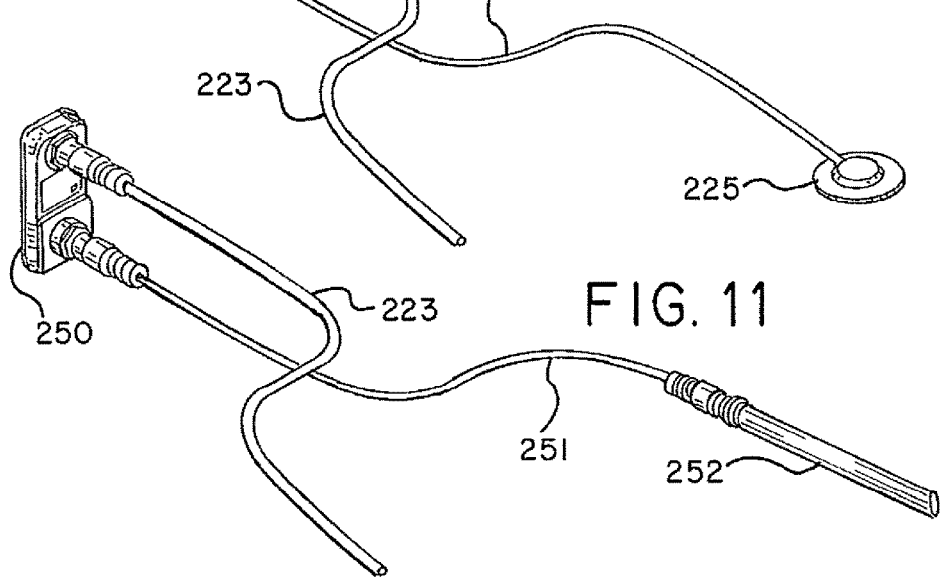
FIG. 10
FIG. 11

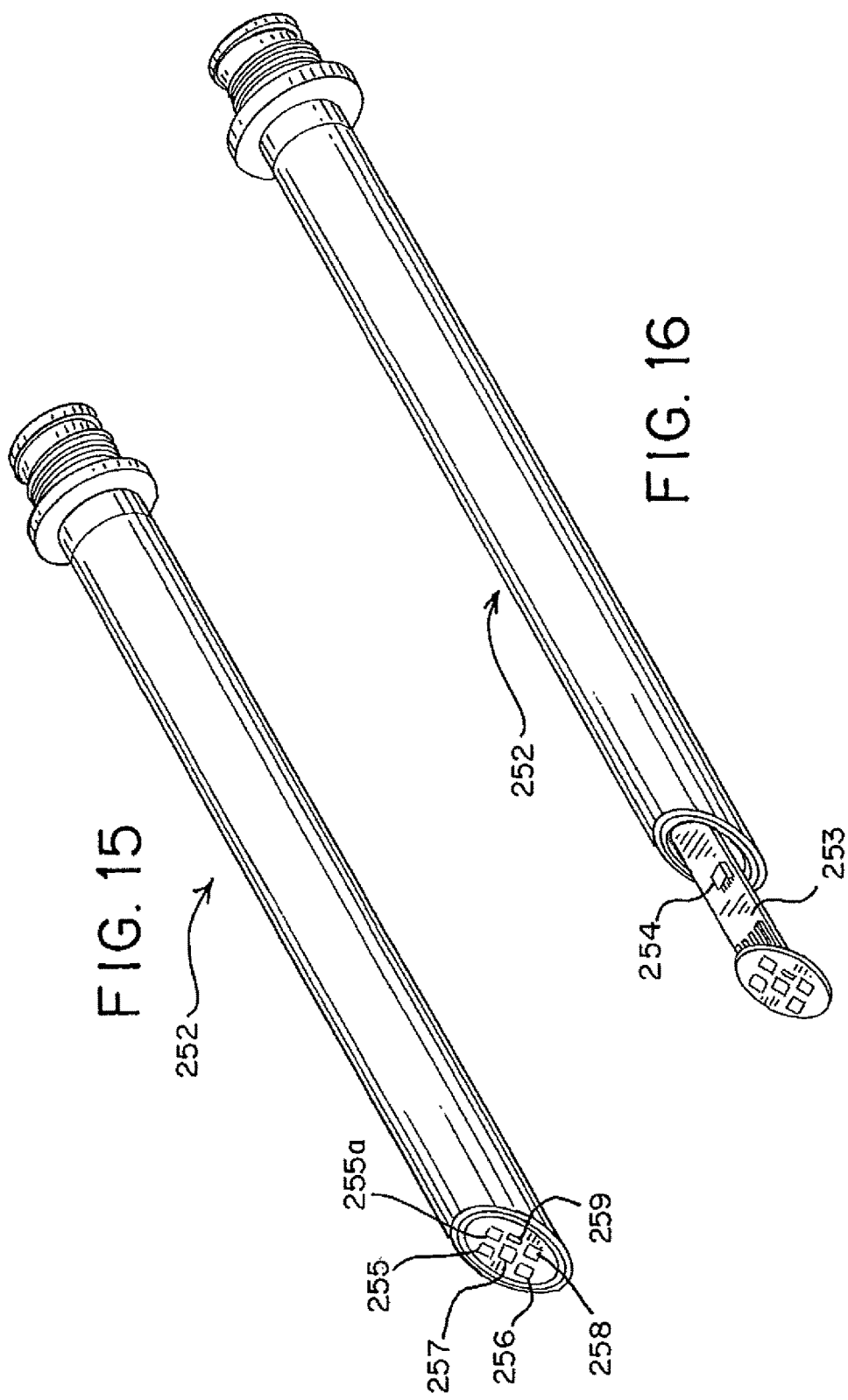

SINGLE-USE SENSORS IN BIOREACTORS, BIOTECH PURIFICATION AND BIOPROCESSING

CROSS-REFERENCE TO RELATED APPLICATIONS

This is a U.S. national stage application of International Patent Application No. PCT/US2014/024353, filed Mar. 12, 2014, and this application claims priority to the provisional application of this International application, namely Ser. No. 61/788,708, filed Mar. 15, 2013. The disclosures of these are hereby incorporated by reference hereinto.

FIELD

This subject matter generally relates to single-use sensors in bioprocessing applications, purification of biotech solutions, bioreactors, and the like, including flow-through disposable cell systems and manifold systems. Same can include the aseptic transfer of solutions out of one or more biological fluid and/or process fluid storage or supply containers. Single-use manifold systems carry out transfers and purification needed in bioprocessing applications. Automated purification and/or dispensing can be accomplished in association with one or more disposable sensors that include pH sensing and can have one or more remotely controlled pinch valves.

BACKGROUND OF THE INVENTION

Good manufacturing practices and governmental regulations are at the core of any pharmaceutical, biotechnology and bio-medical manufacturing process or procedure. Such manufacturing processes and procedures as well as associated equipment must undergo mandated, often lengthy and costly validation procedures. Similar issues exist for sensors when needed in such systems, such as pH sensors, electrical conductivity sensors and oxygen sensors.

For example, the equipment used for the separation and purification of biomedical products must meet stringent cleanliness requirements. The cleaning validation of new or re-commissioned purification equipment (including sensor equipment, bioreactors, and equipment for preparative chromatography or tangential flow filtration—"TFF") may require as many as 50 test-swabs of exposed surfaces and subsequent biological assays of such test-swabs. For a single piece of purification equipment, for example, the associated and reoccurring cost of a single cleaning validation may readily exceed multiple thousands of dollars.

Sterilization is accomplished by exposing to gamma irradiation, or to an ethylene oxide atmosphere. Pre-sterilized, aseptically packaged tube/bag manifolds are commercially available (currently from TC Tech; HyClone; St Gobain Performance Plastics, for example) and are used for the manual transfer of solutions. Typically, manual solution transfer procedures require a technician to operate a peristaltic pump and to manually open and close tube clamps for diverting the solution from the reservoir to the storage bags. Although this procedure reduces the cleaning efforts and cleaning validation expense, operator interaction and time still are required, and these approaches are dependent upon operator expertise for consistent accuracy and precision.

It has been found that, by proceeding in accordance with the present embodiments, significant cost savings and better performance can be realized in a system which incorporates automated, aseptic manifolds and sensors within the field of technology that embraces pre-sterilized, single-use containers, including plastic tubing, containers that can have at least one collapsible portion, bags, bioreactor bags, and flow-through analysis tubes, containers and/or bags, and the components and sensors which contact the biological or chemical fluid can be each pre-sterilized, pre-validated and/or disposable after use.

SUMMARY

An aspect or embodiment includes flow-through, multi-parameter pH/oxygen and pH/conductivity sensors with sensor usage counter. A mechanical flow cell design can be practiced.

In another aspect or embodiment, a pH/conductivity sensor is provided with five electrodes and a thermistor, a pH working electrode, an internal reference electrode, a first conductivity electrode, a second conductivity electrode and a counter electrode or external reference electrode.

In a further aspect or embodiment, a pH/oxygen sensor is offered in three versions, namely, conventional probe/stick design, a flow-through sensor design and a sensor-in-bag design.

Another aspect or embodiment concerns pH/conductivity sensing useful in a single-use preparative chromatography manifold, including a multi-parameter pH/conductivity temperature sensor located in front and/or after the chromatography column.

An additional aspect or embodiment utilizes a sensor-in-bag design useful for single-use bioreactors utilizing either pH/oxygen temperature combination and/or pH/conductivity temperature combination sensors.

A further aspect or embodiment concerns a pH/oxygen/temperature combination sensor located on one or more of the inlet leg or either or both outlet legs of a TFF filter in a manifold system.

Yet another aspect or embodiment concerns a multi-function sensor at one or more locations before or after the column of a normal flow filtration (NFF) column.

An additional aspect or embodiment utilizes a pH/oxygen/temperature combination sensor as well as a pH/conductivity/temperature combination sensor.

In one aspect or embodiment, manifold units include at least one disposable sensor, typically pre-sterilized, making them single-use units which are sterilized and packaged so as to be usable "off the shelf" and address the problem of cleaning and testing at the use site. Generally, same includes tubing lengths, at least one sensor and at least one single-use storage or collection container having multiple inlet and/or outlet passages which are selectively openable and closeable. The tubing lengths can interact with one or more pinch valves which are operable remotely. Remote operation is automated by a controller programmed to carry out procedures according to a selected embodiment.

An aspect or embodiment provides single-use manifolds with at least one sensor for automated, aseptic transfer of solutions in bio-processing, biotech or chemical processing applications.

Another aspect or embodiment provides a single-use tube and/or bag manifold system with integrated multi-parameter sensors designed for biotechnology, pharmaceutical and/or biological industries and laboratories where contamination of biological and/or chemical fluids cannot be tolerated, the sensors being adapted for sterilization by autoclaving or gamma-irradiation.

An aspect or embodiment reduces the need for validation procedures for equipment used in separation and purification of fluids such as in conjunction with the preparation, separation, sensing, analyzing, dispensing and/or reacting of bio-medical or bio-technical products.

Another aspect or embodiment integrates disposable sensors that include a pH determining function with the equipment used in the separation, purification, analysis and/or bioreaction of fluids.

In another aspect or embodiment, sensors and equipment, including manifolds, bags and tubing systems, (typically all disposable for single-time use) are subjected to exposure to various materials, organic fluids and/or treatment conditions that can result in deterioration or change of the equipment, and immediate recognition of such deterioration or change is achieved.

In one aspect or embodiment, serialization and traceability of specific components such as sensors provide product documentation and product traceability. In another aspect, unit product serialization and traceability of biopharmaceutical processing components are provided along with highly time-resolved analytical sensor data that are relevant to product documentation and product traceability, such being provided in connection with sensor-specific data and collection methods and systems.

In yet another aspect or embodiment, single-use sensors are provided that are capable of collecting and storing data digitally and having "read/write" access capability to the on-sensor stored data, such as sensor-specific event logs and flash or data logs having application parameters and/or safety-relevant parameters including, for example, sensor usage time, high pressure exposure events, and sensor gamma sterilization levels.

In a further aspect or embodiment, sensors or components are provided that collect and store data on the sensor or other device, or selected relevant parameters are stored on sensor memory devices together with associated event time stamps.

In yet a further aspect or embodiment, autonomous sensor-specific data collection is accomplished during processing of biopharmaceutical solutions in support of unit product serialization and traceability, including sensor-usage counter-aspects, automated sensor-usage counter-aspects, on-sensor gamma exposure metering aspects, high pressure event detection aspects and device usage diary aspects.

There are several aspects or embodiments of the present subject matter which may be embodied separately or together in the systems and methods described and claimed herein. These aspects or embodiments may be employed alone or in combination with other aspects or embodiments of the subject matter described herein, and the description of these aspects or embodiments together is not intended to preclude the use of these aspects separately or the claiming of such aspects or embodiments separately or in different combinations as may be set forth in the claims appended hereto.

These and other aspects, embodiments, features, improvements and advantages will be understood through a consideration of the following detailed description.

BRIEF DESCRIPTION OF THE DRAWINGS

In the course of this description, reference will be made to the attached drawings, wherein:

FIG. 4 is a perspective view of another embodiment for applying a sensor having pH sensing function and with a single-use flowcell assembly docked or mated to a reusable interface;

FIG. 4A is a perspective view of the embodiment of FIG. 4, with the single-use flowcell assembly "undocked" from the non-disposable, reusable interface;

FIG. 5 is a perspective view of a monitor component of the system that includes and that is in electronic communication with the non-disposable user interface of FIG. 4 and of FIGS. 10 and 11;

FIG. 8A is a bottom perspective view of the single-use flowcell assembly as shown in FIG. 8;

FIG. 10 is a perspective view of a system including a non-disposable interface in communication with a mounting frame for a disposable bag sensor assembly;

FIG. 11 is a perspective view of a system including a non-disposable interface in communication with a single-use probe sensor;

FIG. 15 is a perspective view of another embodiment, same being a single-use probe sensor; and FIG. 16 is an exploded perspective view of the embodiment of 15.

DESCRIPTION OF THE PARTICULAR EMBODIMENTS

As required, detailed embodiments are disclosed herein; however, it is to be understood that the disclosed embodiments are merely exemplary, and specific details disclosed herein are not to be interpreted as limiting, but merely as a basis for the claims and as a representative basis for teaching one skilled in the art to variously employ the subject matter in virtually any appropriate manner.

Fluids processed are variously referred to herein as biotechnology fluids, pharmaceutical fluids, bioreactants, chemical fluids, and so forth. These are understood to be solutions, liquids, gas-including systems, and the like. In general, these are referred to herein as biotechnology fluid or fluids. In the pharmaceutical and biotechnology industries, media preparation departments typically prepare the solutions used in a solution production protocol which follows good manufacturing practices. Media preparation departments are responsible for maintaining solution recipes, preparing and storing buffer solutions and other tasks demanding consistency and accuracy. For example buffer solutions are prepared in large vats, and then pumped through a sterilizing filter, such as one having a porosity of 0.1μ. Typically such solutions need to be filled into presterilized, single use storage bags for later use. A media preparation department may also be responsible for providing inoculating solutions to the operators of a bioreactor. At the completion of a bioreactor batch, the reactor broth can be filled into sterile storage bags for later processing.

Figure 1:
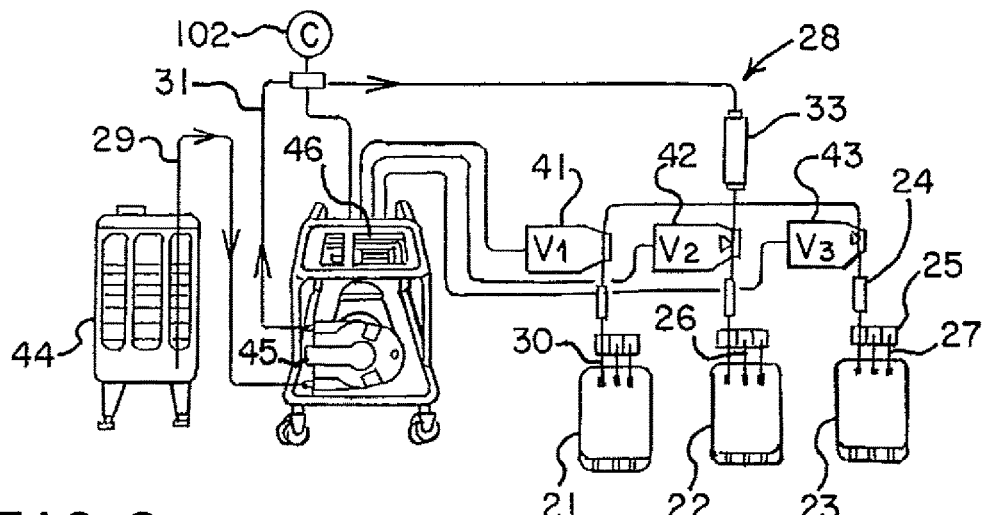
FIG. 1 is an illustration of a single-use system especially suitable for solution transfer, purification and collection in operational association with at least one disposable sensor having pH sensing function.

FIG. 1 shows single-use, pre-sterilized disposable components that are a manifold and transfer tubing assembly and a plurality of bags. As used herein, "single-use" signifies a component that is not intended to be reused, such as for sterilization reasons, without implying it is not possible to reuse the component due to materials or structural limitations. From time to time herein single-use is used interchangeably with "disposable". As used herein disposable does not necessarily mean easily recyclable, biodegradable or the like, but generally indicates same is not intended for multiple, semi-permanent or permanent usage.

A plurality of single-use storage/collection bags 21, 22, 23 are shown, and other types of disposable or single-use containers are suitable. Each container has three tube connections. The primary inlet tubing consists of an aseptic connector 24 and a manual shut-off clamp 25, each of generally known construction. During solution storage, the aseptic connector is covered with an end cap (not shown) to protect the connector 24 from contamination. The manual shut-off clamp 25 is closed during solution storage. These are shown on a first tube connection 30.

The second tube connection 26 in this illustration is connected to the bag with a closed manual shut-off clamp. This tubing and clamp arrangement is used to relieve any gas and/or pressure build-up inside the bag during the filling operation. Another tube connection 27 is identical to the second connection and includes a short piece of tubing and a clamp. This can be used as an auxiliary inlet and/or outlet for recirculation of the bag contents.

A single-use, sterilized manifold and transfer tubing assembly is generally shown at 28. This represents a generalized manifold for automated solution transfer. An inlet end portion 29 of transfer tubing 31 of the unit 28 is for communication with a container, such as a vat, of solution, typically sterile solution.

FIG. 1 also shows a plurality of pinch valves 41, 42, 43 and their respective relative positions with respect to the storage bags. Some or all of the valves can be operated remotely and typically will be pneumatically or electrically activated. A typical set up will have capacity for up to twelve pneumatically actuated pinch valves or more. A like number of storage bags can be accommodated. Relative positions of the pinch valves in association with the optional pressure sensor and the single-use, sterilizing filter are shown. The relative position of the manifold and transfer tubing assembly 28 with the vat 44 and the pump head of a pump unit 45 are shown. Preferably, the pump is a high-accuracy, low-shear peristaltic pump which provides gentle and reproducible bag filling. An example is a Watson Marlow 620 RE peristaltic pump head.

Access to the storage bags is provided via the pinch valves. The pinch valves are normally closed, and typical pneumatic pinch valves require pressurized air (for example 80-100 psi) to open. When such a pinch valve is pressurized, solution is allowed to enter the storage bag while the air in the bag escapes through an integral vent filter. The pinch valve(s) are pneumatic or electrically operated pinch valves (currently available from ACRO Associates, Inc). They are installed external to the tubing and are operated by a multi-valve controller (currently available from Parker-Hannifin), or another computer-based process logic control (PLC) device. The external pinch valves divert the solution inside the manifold without compromising the sterile environment inside the tubing. Diaphragm valves used in other systems are in constant contact with the process solution, whereas pinch valves do not contact the process solution.

Further details regarding the manifold components and their interrelationships are found in U.S. Pat. No. 5,947,689, No. 6,350,382, No. 6,607,669, No. 6,712,963, No. 7,052,604 and No. 7,410,587, as well as U.S. Patent Application Publication No. 2006/0118472. These and all other references noted herein are incorporated by reference hereinto.

The controller can be a stand-alone unit or be associated with another device. In an embodiment, the controller is associated with the pump unit 45. This is shown at 46 in FIG. 1. Whatever form it takes, the controller controls operation of the remotely operable pinch valve(s). The batch filling rate as well as the batch volume delivered into each storage bag is user-programmable via software residing in the controller or accessible by the controller. The controller provides automated bag filling by volume, weight or based on filling time and pump rate.

Figure 2:
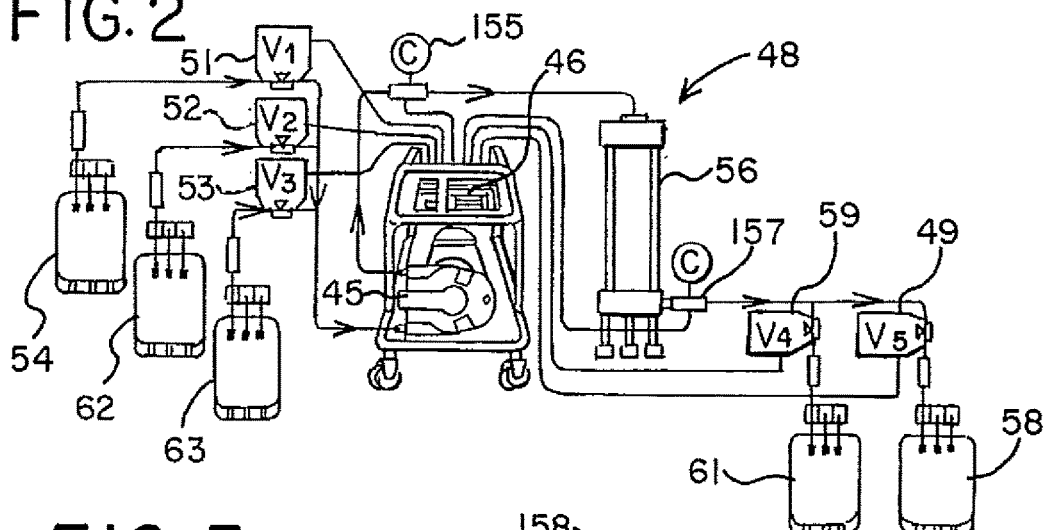
FIG. 2 is an illustration of a single-use system especially suitable for use in automated preparative chromatography in operational association with a disposable sensor having pH sensing function.
Figure 3:
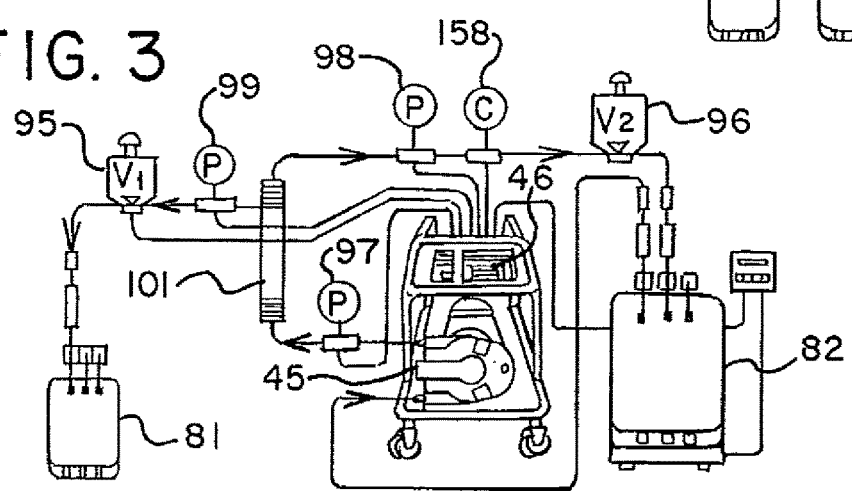
FIG. 3 is an illustration of a single-use system especially suitable for automated tangential flow filtration procedures in operational association with at least one disposable sensor with pH sensing function.
Figure 6:
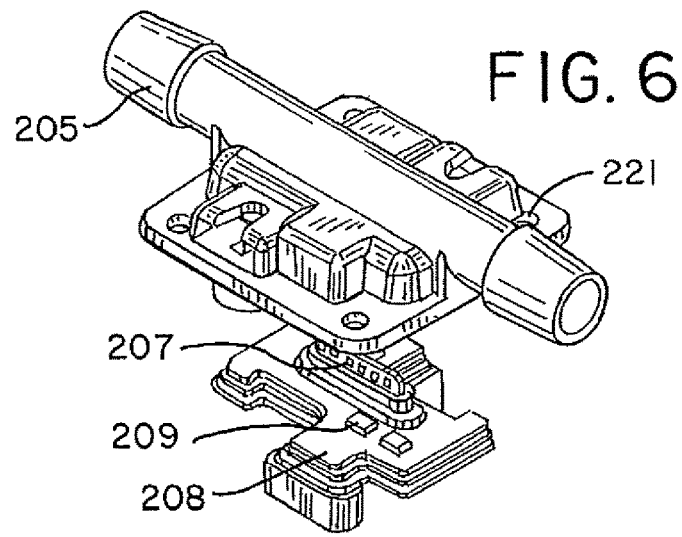
FIG. 6 is an exploded perspective view of the single-use flowcell assembly shown in FIG. 4 and FIG. 4A.
Figure 7:
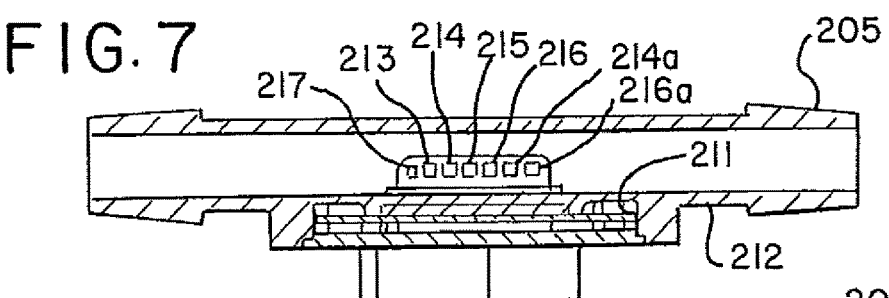
FIG. 7 is a longitudinal cross-section view, in somewhat schematic fashion, along the line 7-7 of FIG. 4 of the flowcell assembly.
Figure 9:
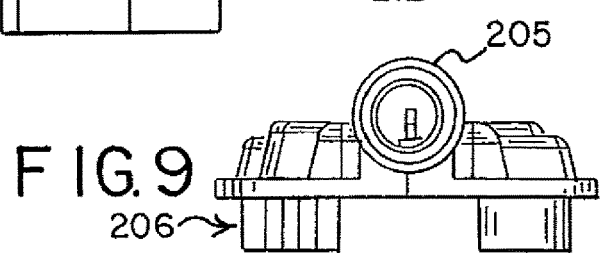
FIG. 9 is an end plan view of the single-use flowcell assembly as shown in FIG. 8.
Figure 8:
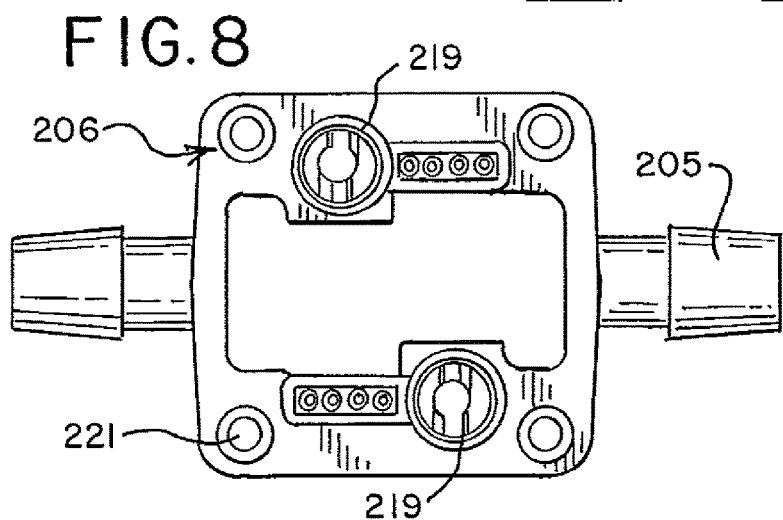
FIG. 8 is a bottom plan view of the single-use flowcell assembly as "undocked" in FIG. 4A.

Typically, an operational program, which can be user-determined, will be provided for the automated filling of storage bags according to FIG. 1, FIG. 2 and FIG. 3. Same are described in the references listed hereinabove.

Another embodiment achieves automated preparative chromatography. In preparative chromatography, process solution containing the bio-molecule of interest is pumped through a column of gel-like particles (stationary phase) suspended in a liquid. The bio-molecule of interest specifically interacts (via ion-ion interactions, hydrophobic interactions, size exclusion, affinity, for example) with the stationary phase thereby retarding the progress of the bio-molecule through the column. Ideally, other dissolved biomaterials will interact only weakly with the stationary phase and thus will exit the column quickly.

The result is a concentration as well as a separation of the bio-molecule from the rest of the process solution matrix. The introduction of an elution buffer will change the local chemical environment of the stationary phase, thereby causing the bio-molecule to be released and thus able to be collected outside the column in a relatively small volume of elution buffer.

In automated preparative chromatography, the column containing the stationary phase first is washed and/or equilibrated with an appropriate buffer solution. This wash and/or equilibration cycle is followed by a loading cycle during which the process solution is pumped through the column. The bio-molecule of interest adheres to the stationary phase. The loading cycle can take many hours, depending on the process solution volume and pump rate with which the solution is pumped through the column. In this embodiment, the loading cycle is followed by a second wash cycle to remove any un-adsorbed biomaterial off the column.

An elution buffer then is introduced to remove the bio-molecule from the column. This removal of the bio-molecule is accomplished either with a step gradient or a linear gradient. After peak collection has been completed, the chromatography column is regenerated and re-equilibrated using appropriate buffer solutions that are generally known in the art.

Such a system is illustrated in FIG. 2. Manifold and transfer tubing assembly 48 represents a generalized manifold for automating preparative chromatography procedures. In operation, and utilizing the controller system, an exemplary pneumatically remotely controlled pinch valve 51 is pressurized and thus opened, thereby providing access to the wash and/or equilibration buffer container 54. At a user-definable pump rate, the wash buffer is pumped through a disposable, in-line 55, through a bubble trap (not shown), through the chromatography column 56, and through a detector or UV flow cell 57. On exiting the flow cell, the wash/equilibration buffer is collected in a waste container or bag while the pinch valve is pressurized and thus open.

During the loading cycle, other pinch valves are remotely opened (typically by being pressurized), while the pinch valves 52, 53 and 59 remain closed. The pump unit 45 pumps the process solution through the manifold system 48, the column 56 and the flow cell 57 and is collected in the waste container or bag 58. In some chromatography applications, the process solution exiting the flow cell needs to be stored separately in a "process receiving bag" (not shown) for possible re-processing. Another pinch valve (not shown) would provide access to such a "process receiving bag" or container.

The loading cycle is followed by a wash cycle (valves 51 and 49 are open/pressurized, all other pinch valves are closed) which carries away any un-absorbed material from the column to waste. By opening pinch valves 53 and 49, elution buffer in bag 63 is introduced into the column and is initially pumped to waste. However, when the signal from the UV detector 57 exceeds a user-defined value, pinch valve 59 is opened thereby providing access to a peak collection bag 61 while valve 49 is closed. On the backside of the eluted peak, valve 59 is again closed, while at the same time, valve 49 is opened.

After the material of interest has been collected in bag 61, the chromatographic column 56 requires regeneration and re-equilibration. The column regeneration process is readily automated via access to appropriate buffer solutions (not shown), which are generally as known in the art. Depending on the underlying chromatographic complexity of the application, access to five or six buffer solutions may be required, and these can be provided in their own single-use bags as desired. Similarly, if multiple product peaks are to be collected, additional peak collection container(s) as well as additional pinch valve(s) may have to be incorporated into manifold and transfer tubing assembly 48.

It will be appreciated that, with this embodiment, sequential scheduling of events are achieved. These include sequential scheduling of wash, load and elution cycles. The controller can initiate buffer selection, loading and peak volume collection. Typical in-line concentration detectors can be Wedgewood UV and/or pH detectors, which have outputs of 4-20 MA outputs which can be monitored simultaneously. A typical pump is a Watson Marlow 620R peristaltic pump head capable of generating 60 psi at a pump rate of 15 liters per minute.

Detection threshold levels are used for valve switching and peak volume collection. These can be user-defined. All solution-handling parameters, such as pump rates, column pressure, and valve positions can be monitored and documented in real time and can be printed out or electronically archived.

In a third embodiment, automated tangential flow filtration is carried out using a modified system designed for this use. Previously referenced U.S. patents and publication disclose the automation of TFF procedures. These are combined with the use of disposable, single-use manifolds, which also include disposable pressure sensors and single-use, collapsible storage bags and the use of remotely operated pinch valve(s).

A typical TFF application that utilizes a single-use, pre-sterilized manifold is shown in FIG. 3, which shows the disposable, pre-sterilized components, including a tubing filtered fluid section having a permeate collection container 81 as well as a process solution container 82 within a filtration flow-through section of the tubing. These are aseptically sealed and in a pre-sterilized for example, irradiated) package. At the beginning of the TFF application, the permeate collection container 81 is empty and has been aseptically connected to the TFF manifold. The process solution container was previously filled, such as by using the system of FIG. 1. The process solution bag 82 is placed onto an optional scale 83 and connected aseptically to the rest of the system. In some applications, weight information can be conveyed to the controller in carrying out the control logic.

Prior to starting the pump unit 45, all of the manual shut-off clamps are opened except those clamps that relieve any gas and/or pressure build-up inside the containers or bags. Initially the valve 95 is closed and the valve 96 is open, while the pump unit 45 starts to recirculate the solution contained in the process solution bag 82 through a tangential flow filter system 101. The air volume contained in the tubing and tangential flow filter system 101 ends up in the process solution bag 82 where it is vented to the outside through a sterilizing air filter (not shown). Once the optimal pump recirculation rate has stabilized, pinch valve 95 is opened and permeate is collected.

The micro filtration or ultrafiltration or purification can be carried out either by constant rate or by constant pressure. Software programs which are suitable to automate the filtration process through the use of the controller 46 and related details are described in U.S. Pat. No. 5,947,689, No. 6,350,382 and No. 6,607,669 and others identified and incorporated by reference herein.

The systems shown FIG. 1, FIG. 2 and FIG. 3 include at least one sensor having pH sensing attributes. When conductivity is a co-function, most available electrical conductivity sensors may be used with these systems, for example, toroidal sensors. The sensor is a pre-sterilized, single-use, disposable, in-line sensor. The embodiment shown in FIG. 3 is a sensor with electrodes.

FIG. 1 shows the aseptic solution transfer system with a disposable in-line sensor 102. During operation, the solution moves from the vat or reservoir 44 through the sensor 102, the filter 33, and then is serially diverted into the single use storage containers, 21, 22 and 23. The pinch valves 41, 42, and 43, as described above, may be included as desired and may be operated remotely to close the lines into each storage bag and typically will be pneumatically or electrically activated.

When the illustrated sensor includes a conductivity sensing component, same monitors the electrical conductivity levels of the solution. The levels are reported back either to a user interface, which displays the information, or to the manifold controller 46. Based on the information provided by the sensor or sensors, the manifold controller 46 (or the user interface in some embodiments) may then modify the operation of the pump unit 45, open and close the various pinch valves, start user-determined programs, and/or stop user-determined programs.

The embodiment generally illustrated in FIG. 2 is utilized to achieve automated preparative chromatography. As stated above, in preparative chromatography, a process solution containing the bio-molecule of interest is pumped through a column of gel like particles (stationary phase) suspended in a liquid. The bio-molecule of interest interacts with the stationary phase while the other bio-molecules in the process solution will quickly exit the column. The manifold and transfer tubing assembly 48 represents the generalized manifold system having an in-line conductivity sensor 155, 157.

The illustrated sensors monitor a parameter and/or parameters of the solution entering the chromatography column 56 and/or the parameter levels as the solution leaves the column. The levels are reported back to a user interface, which displays the information, to the manifold controller 46, or under other electronic approaches. Based on the information provided by the sensors, the manifold controller 46 (or the user interface in some embodiments) may then modify the operation of the pump unit 45, open and close the various pinch valves, start user-determined programs, and/or stop user-determined programs.

The embodiment of FIG. 3 demonstrates how the sensors may be used in conjunction with a system designed to perform automated tangential flow filtration. An in-line sensor 158 is shown here positioned after the pressure sensor 98 and before the pinch valve 96.

The sensors monitor the parameter level or levels of the fluid passing to the process solution bag 82. The levels are reported back either to a user interface, which displays the information, or to the manifold controller 46. Based on the information provided by the sensors, the manifold controller 46 (or the user interface in some embodiments) may then modify the operation of the pump unit 45, open and close the various pinch valves, start user-determined programs, and/or stop user-determined programs. The sensor 158 is useful in TFF as it monitors the concentration, other parameter, or absence of molecules passing through the tubing to the process solution bag 82. For example, if the sensor measures abnormally high electrical conductivity levels during the cleaning or operation of the tangential flow filter, it may signal to the controller or user that the filter is defective. On the other hand, if the sensor measures abnormally low electrical conductivity levels during the cleaning or operation of the tangential flow filter, it may signal that the filter or tubing is clogged.

The preferred embodiment of an in-line sensor has two components: the user interface (e.g., at the controller 46) and the disposable sensor assembly module. Further description of the in-line, single-use or disposable sensor when same is a conductivity sensor is found in U.S. Pat. No. 7,788,047, No. 7,857,506 and No. 7,927,010 and in U.S. Patent Application Publication No. 2009/0180513, entitled "Disposable, Pre-Calibrated, Pre-Validated Sensors for use in Bio-processing Applications," incorporated hereinto by reference. However, in other embodiments, the functionality of each component may be combined with or moved to the other component.

It is possible to provide three separate parameter sensors, namely, pH, oxygen and electrical conductivity parameters. Each sensor typically includes an integral usage counter and a sensor-specific signal and alarm documentation capability. The integration of multiple parameter features (pH/$O_2$ or pH/Conductivity) into one sensor provides important advantages. These are discussed herein and include pH/oxygen combined sensors, pH/electrical conductivity combined sensors, pH/oxygen/temperature combined sensors and pH/electrical conductivity/temperature combined sensors.

Metal deposition onto a silicon electrode substrate and subsequent surface oxidation provides an excellent base for immobilizing redox-active reagents required for a hydrogen ion selective electrode response. Transition metals such as nickel, silver, gold, and platinum and their respective oxides have been used successfully in electrode surface derivation reactions. The use of a silicon substrate is desirable for pH sensor production. Integration of a thermistor function can be into a pH sensing chip.

The continuous monitoring of dissolved oxygen is of great significance in mammalian and microbial cell cultures. Simplicity and reduced cost are examples of benefits of monitoring both pH and oxygen simultaneously on the same electrode. Similar to the pH sensing technology, surface immobilized, redox-active reagents can be used in the determination of oxygen by voltammetry. A further advantage of combining pH and oxygen function is the use of a common reference electrode for the two analytical parameters.

The continuous monitoring of pH and electrical conductivity is of significance in chromatography, tangential flow filtration (TFF) as well as in some normal flow filtration (NFF) applications.

The embodiment of FIG. 4, FIG. 4A, FIG. 6, FIG. 7, FIG. 8, FIG. 8A and FIG. 9 includes a single-use flow through sensor assembly, generally designated 201, and a non-disposable interface 202. The interface has components to communicate data and like between the interface and a monitor 203 shown in FIG. 5. Interface 202 has a docking location 204 having members to securely attach, in detachable fashion, the flowcell assembly 201.

The disposable or single-use flowcell assembly module 201 contains inexpensive components. Typically, the flowcell assembly module contains a short tubular fluid conduit 205 and a sensing portion, generally designated as 206, which includes electrodes 207, a printed circuit board (PCB) 208 and a sensor-embedded non-volatile memory chip 209, such as a FRAM memory chip. In this embodiment, six electrodes are positioned on the disposable flow cell and in an opening 211 in the fluid conduit wall 212, and are placed in the pathway of fluid progressing through the system that is connected at both ends of the fluid conduit 205. The electrodes connected or sealed into place to prevent leaks or contamination.

The illustrated electrodes can include one or more of a pH working electrode 213, a first external reference electrode 214, a pH reference electrode 215, a conductivity or oxygen working electrode 216, a second external reference electrode 214*a*, a conductivity or oxygen reference electrode 216*a*, and a thermistor 217. Usually, at least two such electrodes are included and/or are activated for a given intended use.

When a conductivity electrode is used, same can take the form of a toroidal conductivity sensor. The toroids of the toroidal sensors may be arranged in a non-obtrusive manner around the fluid circuit. Typically, two toroids are used. One toroid is used to "drive" or induce a current through the fluid, while the other "senses" or measures the induced current through the fluid.

The electrodes or toroids are connected to the PCB 208. The PCB may contain various components, such as the thermistor to measure the temperature of the fluid in the fluid circuit or a non-volatile memory chip or EEPROM. The PCB is connected to a user interface, control unit, or controller or monitor 203. The monitor 203 with user interface and non-disposable interface 204 connects to each other by a wires or lead assembly 217 in this illustrated embodiment. As seen in FIG. 8A, connectors 218 are in the sensing portion or housing 206 for making electrode connections. Spring-loaded screws 219 releasably secure the disposable flow cell 201 to the docking location 204 of the non-disposable interface. A plurality of holes 221 receive a decorative hood (not shown).

The monitor 203 typically includes a controller and the user interface. The selected parameter components are monitored. For example, when the sensor has conductivity components, same produces the current that drives the electrodes or toroids and measures the conductivity by measuring the current on the "sensing" electrodes or toroids. The electrical conductivity of the fluid passing through the fluid conduit 205 is measured by driving a current through one or more of the electrodes. For example, one can then use the remaining electrodes to measure the current that passes through the fluid. The current or the voltage drop measured is proportional to the conductivity of the fluid passing through the fluid conduit.

The user interface or monitor 203 may access calibration information stored in the non-volatile memory of the sensor. During production of the disposable sensors, small variations in the design and placement of the electrodes therein as well as variations in the accuracy of the thermistors may lead to inaccurate parameter measurements. However, each sensor is individually calibrated to account for the adverse effects due to these small variations. The sensor specific calibration information is stored in the non-volatile memory of the sensor.

This calibration information may include a temperature offset and a parameter constant, such as a pH, oxygen or conductivity constant. The temperature offset, for example utilizing thermistor data, represents the linear difference between the known temperature of the fluid and the temperature measure by the sensor at the time of calibration. For example, when conductivity is monitored, the conductivity constant represents the difference between the known conductivity of the fluid and the conductivity measure by the sensor at the time of calibration. When measuring the conductivity of the fluid in the fluid conduit, the user interface or controller of the monitor 203 will retrieve the calibration information to use in the calculations for conductivity (or other parameter). The temperature offset and parameter constant are later utilized by the user interface or controller to calculate the actual parameter value of the biotechnology fluid passing through the fluid conduit of the sensor.

The calibration information may also include information about the method of calibration, the statistical variance among different sensors in the same lot, and the date when the sensor was last calibrated. In addition to the calibration information, production information may be stored in the non-volatile memory on the sensor. Production information may include items such as the date, time, or lot number for when the sensor was manufactured.

FIG. 10 shows an embodiment of a non-disposable user interface, as generally designated 220. The user interface 220 can be somewhat more portable in comparison to an entire manifold system or monitor 203, may be utilized separately from the entire system, and allows for either the user interface or components of the system to be independently upgraded or replaced.

Non-disposable user interface 220 is connected, such as by a cable 223 to the monitor 203 and by a second cable 224 to a disposable bag sensor, generally designated at 225. Single-use sensor 225 typically includes a circuit board 226, a FRAM memory 227 and the electrodes 228, which typically are as described herein and can include pH, oxygen, temperature and/or conductivity sensing capabilities. These components are mounted suitably such as on a mounting frame 229 and protected by a cap 230.

Figure 12:
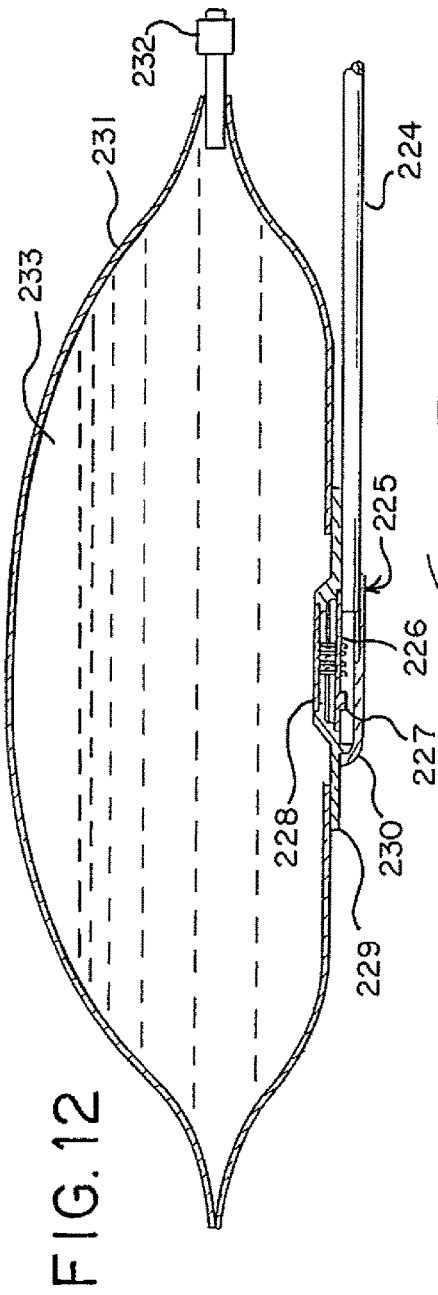
FIG. 12 is a somewhat schematic, cross-sectional view of a bioreactor bag secured to the mounting frame of FIG. 10.

In this embodiment, a bioreaction bag 231 is shown in FIG. 12, having an access port 232 as generally known in the art. In a typical application, the bag contains solution, such as bioreactants that are undergoing changes that are monitored by the disposable bag sensor 225. A quantity of air or oxygen or other gas can be within the headspace 233 of the bag.

Figure 14:
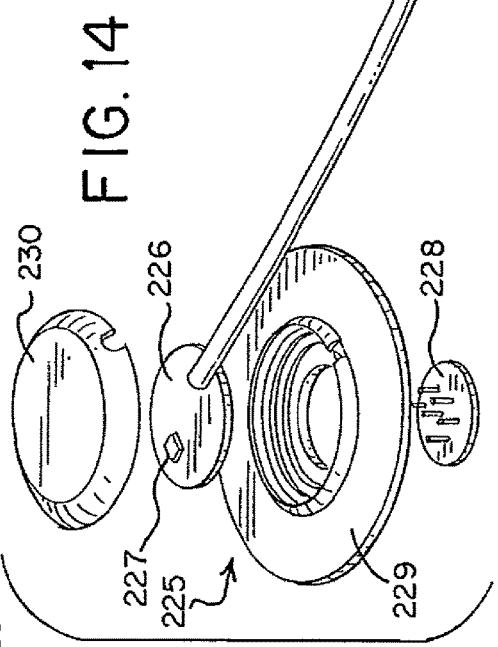
FIG. 14 is an exploded perspective view of the mounting assembly of FIG. 13.
Figure 13:
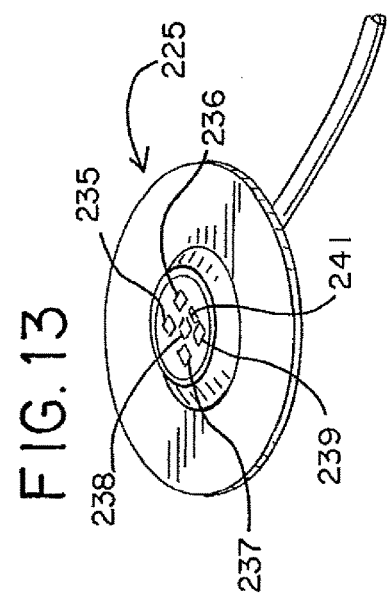
FIG. 13 is a perspective view of the mounting assembly for the bioreactor bag of FIG. 12.

Further details of the bag sensor 225 are found in FIG. 13 and FIG. 14. The illustrated electrodes can include one or more of a pH working electrode 235, a pH reference electrode 236, a conductivity or oxygen working electrode 237, an external reference electrode 238, a conductivity or oxygen reference electrode 239, and a thermistor 241. Usually, at least two such electrodes are included and/or are activated for a given intended use.

FIG. 11 has a non-disposable interface 250, cable 223 and an elongated connector 251 such as a cable for releasable connection with a disposable probe sensor, generally designated at 252, which can be used for checking and monitoring parameters of solutions or fluids in an accessible environment apart from a flow tube or a bioreactor bag.

Disposable probe sensor assembly 252 is seen in FIG. 15 and FIG. 16 and has an elongated probe body tethered by way of the connector 251 at a proximal end portion of the elongated probe. Probe sensor assembly 252 includes a circuit board 253, a memory component 254 such as a FRAM and electrodes and monitoring members. Examples are one or more of a pH working electrode 255, a pH reference electrode 252, a conductivity or oxygen working electrode 256, an external reference electrode 257, a conductivity or oxygen reference electrode 258, and a thermistor 259. Usually, at least two such electrodes are included and/or are activated for a given intended use.

The user interface of the monitor 203 has a display 222 and several input keys on its face. Typical keys can include a Menu key, an Up key, a Down key, a Re-Cal key, an Enter key, an Exit key and a Sensor On/Sensor Standby key. For example, to turn the user interface on, the Sensor On key could be activated. During normal operation, the display 222 typically reports the parameter or parameters of the fluid being measured by the system in an appropriate unit, such Siemens for electrical conductivity, the temperature of the fluid in degrees Centigrade, the percent of a parameter such as total conductivity, and a graphical representation.

The Menu key allows users to progress through different menus. As an example, the display screen can initially present a "RUN" screen, which can for example display the conductivity, pH and/or oxygen level of the fluid being measured by the system, the temperature of the fluid in degrees Centigrade, the percent of a total for each parameter, and a graphical representation of the percentage. As an example, in a possible set-up, if the user repeatedly presses the Menu key, the screen will display the High Conductivity Value (for example 80,000 μS) and then the Low Conductivity Value (for example 0 μS). If the user continues to press the Menu Key, the user interface will display the calibration information retrieved from the non-volatile memory of the sensor.

The user interface does not necessarily have to use the calibration information stored on the sensor. In the illustrated embodiment, the user may modify the calibration information utilized by the user interface without permanently modifying the information stored in the non-volatile memory on the sensor. The user may manually change the calibration information utilized by the user interface by selecting the Up or Down arrow keys when presented with the corresponding screen.

The modifiable calibration information may include the Reference Temperature, the Temperature Coefficient, and the Temperature Offset. As an example, by pressing the Menu Key, the user may modify by using the Up or Down arrow keys the units in which parameter is displayed, the setting for the serial port, the different print times for the print option, the maximum conductivity measurement at which point the user interface produces a high audible alarm or low audible alarm. The user may also select to restore or re-install the factory calibration values, or change the date and time. When presented with any of the above mentioned options, the user may return the user interface to normal operations without changing the option by pressing the Exit Key.

The user may also re-calibrate the sensor or overwrite the calibration information stored in the non-volatile memory chip by selecting the Re-cal key, which runs the recalibration program. As an example, the recalibration program displays the calibration information on the display screen. The user can scan through the calibration information by using the Up and Down arrow keys. By pressing the Menu key, the user may select a specific piece of calibration information, such as the Pump Low Calculation solution, External Calibration Data, and the High Pump Calibration. The user may then modify the value for each piece of calibration information by selecting the Up or Down keys.

After the information is modified, the new value overwrites the stored information in the non-volatile memory of the sensor when the user presses the Enter Key. As an example, the display will then report the current readings as computed using the new calibration information. In the future, when the user selects "Factory Reset", the current settings of the user interface are replaced with those values entered by the user during the last recalibration program. However, if the user wants to end the recalibration program without changing the options, he or she need only press the Exit key.

The user interface may also include a sensor key (not shown). As an example, when the user presses the Sensor key, the user interface retrieves the production information and parameter information stored in the non-volatile memory of the sensor. The parameter information may include information that was replaced by the recalibration program. Initially, this operation can display a unique ID number for the sensor. By pressing the Menu key, the user may view other calibration information, such as the type of solution used during calibration as shown, the temperature of the calibration solution, and the statistical information for the sensor. The user may also view the date when the sensor was last calibrated or recalibrated. The user may return the user interface to normal operations by pressing the Exit Key.

Embodiments of traceability of single-use sensors to National Institute of Standards Technology (NIST) standards include access to the following information: sensor material and manufacturing processes, sensor-specific calibration factor, and sensor lot number. Factory pre-calibrated single-use sensors provide certified sensor calibration and performance data. Also available are stable on-sensor storage of sensor identification number, calibration data and/or lot number. The system allows hook up to a monitor for verification and display of sensor-specific information. In-field sensor calibration issues are avoided, and single-use sensors are easily integrated into purification manifolds prior to sterilization, such as by autoclaving or gamma irradiation.

In an embodiment, electronic sensor-specific traceability is achieved using an on-sensor read/write memory chip. An alternative is to provide sensor calibration information in bar coded or other machine-readable format. Use of a ferroelectric random access memory (FRAM) memory chip provides gamma radiation stability. Sensor-specific traceability is sufficiently adaptable to meet unit level product serialization and traceability requirements of governmental agencies or jurisdictions.

In an embodiment, metrology-based usage control is provided in connection with sensor usage. For example, pressure sensors provide on-sensor usage counters. In other approaches, RFID-augmented single-use sensors for gamma-irradiated pre-packaged manifolds are provided. Such RFID approach permits confirming sensor calibration data without opening a sterilized bag containing the sensor, such as after having undergone gamma irradiation. Also noted are dual single-use sensor configurations having improved sensor performance and robustness.

The present subject matter addresses autoclaving-related performance issues. These include thermally induced cracking of plastic and leaking of sensors. Leaking pressure sensors having less than 30 psi pressure can correspond to degraded pressure performance. Another problem addressed is a non-functional sensor caused by insufficient drying after autoclaving. A performance audit of autoclaved sensors can involve high-performance plastics and adhesive epoxies used in sensors. Same are to be USP class VI compliant, stable at 123° C. autoclave temperature, and the polymer and adhesive in the assembly should have similar expansion coefficients. Often, polypropylene and polycarbonate are inappropriate materials for use in autoclaved sensors. Desiccating μ-filters afford timely removal of steam condensate from sensor and tube manifolds.

As discussed in more detail herein, by proceeding as presently disclosed, gamma irradiation of sensors and of tube manifolds is a cost-effective alternative to autoclaving. The present approach addresses gamma-related performance issues including the following. Excessive gamma radiation (for example, in excess of 45 kGy) can degrade polymer materials, typically accompanied by an increase in extractable and leachable components. Gamma irradiation of silicon-based memory chips will destroy all memory content, resulting in non-functional memory. According to testing, sensor polymer material and electronic components should remain functional after exposure to from between about 25 and about 45 kGy. FRAM chips are gamma stable up to 45 kGY; however, chip supply voltage should be raised to 5.5 volts for such a chip to remain functional at higher gamma irradiation levels.

A sensor usage counter is of considerable utility since it provides a time and performance history or a specific sensor from installation to de-commissioning of the sensor. The sensor usage counter is initialized by a threshold event, which can be visualized when connected to a monitor. When the sensor has a thermistor function, the threshold event will occur when used in an oscillating RC circuit in which event the thermistor will be heated in a sinusoidal fashion. The frequency of the heating cycle will depend on the capacitance (C) and the thermistor resistance (R). Because of the large thermal conductivity differences, the thermistor heating frequency in air will be considerably greater than in water. Thus, measuring this frequency shift provides contextual sensor usage information to be stored in the sensor's memory device together with sensor ID and calibration factors. When desired, this threshold event is counted as sensor "use" after persisting for a certain time period. In an embodiment, the specific sensor usage and associated time intervals are stored in the on-sensor memory device.

In a further embodiment, the total accumulated sensor usage time also can be pre-selected, for example, 100 hours. The elapsed usage time, as well as the remaining usage time, typically are updated at regular intervals, and when the sensor is connected to a monitor, such is visible by the monitor. Such data are stored in the on-sensor memory. The remaining time will be displayed on the monitor when provided, and an alarm will be signaled when the preselected total usage time has been obtained. At this point, the sensor usage counter, when provided with input provisions for disabling the sensor, continued sensor usage will be prevented.

Alternatively, an override feature can be provided that allows continued use of the sensor, such as by authorized personnel having a password-protected opportunity to intervene and set limits on sensor usage.

At times it is desired to subject sensors, tube manifolds and other devices and components used in processing of biopharmaceutical solutions to be subjected to gamma irradiation for generating sterility conditions for such devices and components. However, excessive irradiation can cause damage to polymer materials of the devices or components, resulting in undesirable increase in leachables and extractables. The present subject matter allows one to determine and document gamma exposure level prior to distribution, commissioning or use of such sensors, tube manifolds or other devices or components.

The present approach makes use of FRAM devices which have been determined to survive gamma irradiation levels in excess of 45 kGy. Gamma irradiation of the FRAM memory devices is accompanied by an increase in the threshold voltage of the FRAM. The average pre-gamma threshold voltage is 4.25 (+/−0.050) volts, whereas the average post-gamma irradiation threshold voltage is measured at 4.75 (+/−0.250) volts. This difference can be used as a qualitative (yes/no) gamma irradiation indicator that the sensor or the like had been subjected to gamma irradiation.

This difference between pre- and post-gamma irradiation threshold levels can be used as a quantitative gamma-level meter. For example, the sensors or the like being evaluated are exposed to a controlled, i.e., known, gamma irradiation level. Such known levels are certified and published. By the approach of the present disclosure, the published gamma exposure data, together with the corresponding measurement of the average post-gamma irradiation threshold voltage is used to generate a two-point calibration curve that is stored in the sensor-specific FRAM memory device.

The two-point gamma-exposure calibration curve correlates the average, low-level pre-gamma threshold voltage of 4.25 V with a 0 kGy gamma-irradiation level whereas the average, high-level threshold voltage of 4.75 V is correlated with a 35 kGy (+/−5%) gamma-irradiation level if the certified gamma-irradiation was carried at 35 kGy. If the gamma-irradiation level is certified at some other level, then the certified level is correlated with the corresponding post-gamma average threshold voltage.

As an example, a FRAM chip can have a factory-specified supply voltage requirement of 5.00 Volts. The affected FRAMs would not be functional at a specified 5.00 Volt supply voltage. However, as has been determined in this disclosure, a supply voltage greater than the highest indicated threshold voltage will restore FRAM functionality. Thus a supply voltage between 5.250 and 5.500 Volts would safely ensure FRAM functionality at all indicated gamma-exposure levels. This is the basis for an electronically verifiable gamma-exposure meter as outlined herein.

When a sensor is connected to a monitor, the gamma-exposure level stored in the sensor-specific memory device is displayed by the monitor indicating either a zero kGy gamma exposure level for a non-gamma-irradiated sensor or a positive kGy number that substantially coincides with the actual gamma exposure level for that sensor.

The control logic of the controller can determine the extent of filling of one or more of the single-use containers by processing data monitored by the system to achieve filling of the single-use bag by volume, by weight, or by flow rate and filling time. When desired, the control logic can be operable to activate flow of the biotechnology fluid and open a first remotely operable pinch valve for a length of time needed to flow a selected volume or weight of biotechnology fluid into a first single-use container associated with a first remotely operable pinch valve. The control logic also can be operable to activate flow of the biotechnology fluid and open a second remotely operable pinch valve for a length of time needed to flow a selected volume or weight of biotechnology fluid into a second single-use container associated with the second remotely operable pinch valve, and wherein said control logic is operable to activate flow of the biotechnology fluid and opens a further remotely operable pinch valve for a length of time needed to flow a selected volume or weight of biotechnology fluid into a third said single-use bag associated with the third remotely operable pinch valve until a user-selected number of single-use containers are filled.

Further, the control logic can be operable to activate flow of the biotechnology fluid and open one of the pinch valves for a length of time needed to flow a selected volume or weight of biotechnology fluid into a single-use container associated with that pinch valve. The control logic also can be operable to activate flow of the biotechnology fluid and open another of the pinch valves for a length of time needed to flow a selected volume or weight of biotechnology fluid into another pinch valve until a user-selected number of single-use containers are filled.

An outlet end portion of the manifold tubing can have a plurality of serially arranged outlet passageways each having a connector for operable connection with one of the single-use containers, and one of the pinch valves can control passage of the biotechnology fluid from the tubing to the single-use container. Also included can be a single-use separation component selected from the group consisting of a separation unit, a purification unit, a sterilizing filter and a combination thereof positioned along said length of tubing such that the biotechnology fluid can flow therethrough at a location upstream of said outlet end portion. The disposable sensor having a pH function is positioned along the length of tubing such that the biotechnology fluid can flow therethrough at a location upstream of the outlet end portion. When desired, at least one disposable pressure sensor positioned along said length of tubing such that the biotechnology fluid can flow therethrough at a location selected from the group consisting of upstream, downstream and both upstream and downstream of the single use separation component and upstream of said outlet end portion.

When the manifold system is for automated preparative chromatography, the tubing typically is in at least two sections including a chromatography feed section and a chromatographed fluid section, and the chromatography feed section has an outlet and a plurality of serially arranged inlet passageways each having an aseptic connector operably connected with one of said single-use containers, wherein the chromatographed fluid section has an inlet, and the outlet end portion of the tubing has a plurality of serially arranged outlet passageways each having an aseptic connector operably connected with said single-use container. A disposable pressure sensor can be positioned along said tubing chromatography feed section such that the biotechnology fluid can flow therethrough at a location upstream of said outlet end portion and a chromatography column between the outlet of the chromatography feed section of the tubing and the inlet of the chromatographed fluid section of the tubing.

When the manifold system is for tangential flow filtration, one of the single-use bags is a process solution bag and another single-use bag is a permeate collection bag, wherein the tubing is in at least two sections including a filtration flow-through section and a filtered fluid section, the filtration flow-through section including the process solution bag. The filtered fluid section includes the permeate collection bag. A disposable filter is between the filtration flow-through section and the filtered fluid section, whereby fluid from said process solution container can be filtered through said disposable filter and collected in said permeate collection container. The inlet end can be within the filtration flow-through section and in operative communication with the process solution single-use bag, said filtration flow-through section further includes a recirculation length having one of the pinch valves between an exit port of the disposable filter and the process solution single-use container.

The TFF system can further include a disposable pressure sensor positioned along the filtration flow-through section tubing such that the biotechnology fluid can flow therethrough at a location upstream of said disposable filter. In addition, a disposable pressure sensor can be positioned along the filtration flow-through section tubing such that the biotechnology fluid can flow therethrough at a location downstream of the disposable filter. When desired the disposable pressure sensor is positioned along the filtered fluid length of tubing such that the biotechnology fluid can flow therethrough at a location between the disposable filter and the permeate collection single-use bag.

A manifold and flow imparting system for biotechnology uses in tangential flow filtration includes a manifold unit which is pre-sterilized and disposable so as to be adapted for single-time usage, including: at least one length of tubing having at least one inlet end portion, at least one outlet end portion, an outside surface, and an inside surface which is sterilized for passage of a biotechnology fluid therethrough. Also included are a plurality of single-use containers, each having an access port, one said single-use bag is a process solution bag and another said single-use bag is a permeate collection bag. The tubing is in at least two sections including a filtration flow-through section and a filtered fluid section, said filtration flow-through section includes said process solution bag, said filtered fluid section includes said permeate collection bag, an aseptic connector operatively connects the length of tubing with the single-use bag. A disposable filter is between the filtration flow-through section and the filtered fluid section, whereby fluid from said process solution bag can be filtered through said disposable filter and can be collected in said permeate collection bag. At least one single-use sensor having at least a pH sensing function is positioned in the system, typically along the tubing, usually along a flow-through portion of the tubing.

At least one valve such as a pinch valve is remotely operable in response to a signal remote from the valve, each valve being located so as to engage the outside surface of the length of tubing at a discrete location along the tubing at which each respective valve is located. Each valve independently selectively allows or stopping flow of the biotechnology fluid through said inside surface of the length of tubing at said discrete location for that valve, which flow is imparted by a flow imparting unit at a selected location upstream of the disposable filter.

An automated manifold and flow imparting system for biotechnology uses in automated preparative chromatography includes a manifold unit which is pre-sterilized and disposable so as to be adapted for single-time usage, including at least one length of tubing having at least one inlet end portion, at least one outlet end portion, an outside surface, and an inside surface which is sterilized for passage of a biotechnology fluid therethrough, a plurality of single-use containers, each having an access port, and a plurality of aseptic connectors that operatively connect said length of tubing with said single-use bag. The tubing is in at least two sections including a chromatography feed section and a chromatographed fluid section, the chromatography feed section has an outlet and a plurality of serially arranged inlet passageways each having one of the aseptic connectors operably connected with said single-use bag. The chromatographed fluid section has an inlet, and the outlet end portion of the tubing has a plurality of serially arranged outlet passageways each having one of said aseptic connectors for operable connection with one of said single-use containers. The manifold unit has at least one single-use sensor having at least a pH sensing function.

A plurality of pinch valves or other type of valves, at least one of which is remotely operable, are part of the automated system, and each valve engageable with the length of tubing at a discrete location, for example its outside surface, along the tubing at which each respective valve is located. Each valve independently selectively allows or stops flow of the biotechnology fluid through the inside surface of the length of tubing at the discrete location for that valve. A first said valve controls passage of the biotechnology fluid from one of the single-use containers to the chromatography feed section, and a second said valve controls passage of the biotechnology fluid from the tubing chromatographed fluid section to the single-use bag of the chromatographed fluid section. A chromatography column between said chromatography feed section and said chromatographed fluid section, and a flow imparting unit is at a selected location upstream of the chromatography column. A controller controls operation of the flow importing unit, such as a pump unit and of each remotely operable valve, the controller having control logic which dictates opening and closing of said remotely operable valve.

The automated systems in accordance with this disclosure include having the control logic of the controller dictate the rate of flow imparted by the flow imparting unit. The control logic of the controller typically determines the extent of filling of the single-use bag by processing data monitored by the system to achieve filling of the single-use bag by volume, by weight, or by flow rate and filling time.

When the automated system is for preparative chromatography, the control logic has a loading cycle which activates the flow imparting unit and opens a first and a second remotely operated valve, the first remotely operable valve is upstream of the chromatography column and controls egress of process solution from a container thereof. A second remotely operable valve is downstream of the chromatography column and controls access to a first single-use bag. The loading cycle of the control logic precedes an elution cycle which opens a third remotely operated valve which is upstream of the chromatography column and controls egress of elution solution from a container thereof and into and through the chromatography column. In an embodiment, the control logic has a peak value collection cycle which activates a fourth remotely operated valve which is downstream of the chromatography column and controls access of solution into a second single-use bag. For example, when closed, the fourth remotely operated valve denies access to the second single-use bag, when commanded to do so by the control logic, to provide a wash cycle.

In such an automated system for preparative chromatography, a detector downstream of said chromatography column can be provided to monitor flow out of the chromatography column for a peak collection value. In this arrangement, the and wherein said control logic receives peak collection value data from the detector for use in said peak value collection cycle. Typically, a detector downstream of the chromatography column monitors flow out of the chromatography column for a peak collection value; and the control logic receives peak collection value data from this detector for use in the peak value collection cycle. In an embodiment, the peak value collection data include a threshold value start of peak collection and a threshold value end of peak collection. In an embodiment, the threshold value start of peak collection is a positive slope signal, and wherein said threshold value end of peak collection is a negative slope signal.

When the automated manifold and flow imparting system for biotechnology uses is for tangential flow filtration, same includes a manifold unit which is pre-sterilized and disposable so as to be adapted for single-time usage, the tubing is in at least two sections including a filtration flow-through section and a filtered fluid section. The filtration flow-through section includes a process solution bag, and the filtered fluid section includes a permeate collection bag. A disposable filter is between the filtration flow-through section and the filtered fluid section, whereby fluid from the process solution bag is filtered through the disposable filter and is collected in the permeate collection bag. At least one single-use sensor having at least a pH sensing function is positioned in the system, typically along a flow-through portion of the tubing.

At least one valve, such as a pinch valve, is remotely operable in response to a signal remote from the valve, the valve engageable with the outside surface of the length of tubing at a discrete location therealong for that valve. A flow imparting unit at a selected location upstream of the disposable filter, and a controller operatively controls the flow imparting unit and the valve or valves, the controller having control logic which dictates opening and closing of the remotely operable valve or valves and dictates the rate of flow imparted by the flow imparting unit.

In an embodiment, the automated system includes at least one detector positioned along a location downstream of the disposable filter for monitoring a parameter of the fluid within the tubing and for transmitting data on the parameter to the controller, wherein the control logic receives the data from the detector and monitors the flow of fluid through the filtration flow through section of the tubing until an optimal recirculation parameter is achieved, at which time said control logic signals that the filtration flow through section of the tubing is to be blocked by closing one of the valves and signals that the filtered fluid section of the tubing is to be unblocked by opening another of the valves, whereby filtered fluid begins to flow into said single-use permeate collection bag. In an embodiment, the detector is a pressure sensor, wherein the recirculation parameter is fluid pressure, and the control logic receives data from the pressure sensor to determine when optimum recirculation pressure is achieved.

In an embodiment, the control logic directs the flow imparting unit to modify its flow imparting rate in response to changes in pressure at the pressure sensor so as to maintain a substantially constant selected rate imparted to the fluid by the flow imparting unit and thereby assist in achieving said optimum recirculation pressure. In another embodiment, the detector is a fluid flow rate sensor, the recirculation parameter is fluid velocity, and the control logic receives data from the fluid flow rate sensor to determine when optimum recirculation fluid velocity is achieved. A further embodiment has the control logic direct the flow imparting unit to modify its flow imparting rate in response to changes in flow rate at the fluid flow rate sensor so as to maintain a substantially constant selected flow rate imparted to the fluid by the flow imparting unit and thereby assist in achieving optimum recirculation pressure.

Another manifold system for biotechnology uses is for single-time usage in an automated, aseptic biotechnology solution transfer system. This includes at least one length of tubing having at least one inlet end portion, at least one outlet end portion, an outside surface, and an inside surface which is sterilized for passage of a biotechnology fluid therethrough, at least one single-use bag having an access port, at least one single-use sensor having at least a pH sensing function, and at least one valve such as a pinch valve remotely operable to engage the outside surface of the length of tubing. In an embodiment, the transfer system further includes a flow imparting unit at a selected location upstream of the valve and a controller having control logic which dictates the timing of opening and closing of the remotely operable pinch valve, and wherein the control logic of the controller also dictates the rate of flow imparted by said flow imparting unit, such as a pump or an automated pump. The control logic of the controller can determine the extent of filling of the single-use bag by processing data monitored by the system to achieve filling of the single-use bag by volume, by weight, or by flow imparting rate and filling time.

In an embodiment, the control logic is operable to operate a multiplicity of valves, for example pinch valves. The control logic activate flow imparting action of the flow imparting unit and to open a first remotely operable valve for a length of time needed to flow a selected volume or weight of biotechnology fluid into a first single-use bag associated with the first remotely operable valve, wherein the control logic is operable to activate flowing action of said flow imparting unit and to open a second remotely operable valve for a length of time needed to impart flow of a selected volume or weight of biotechnology fluid into a second single-use bag associated with the second remotely operable valve, and wherein said control logic is operable to activate flow imparting action of the flow imparting unit and to open a further remotely operable valve for a length of time needed to impart flow of a selected volume or weight of biotechnology fluid into a third said single-use bag associated with the third remotely operable valve until a user-selected number of single-use containers are filled.

In an embodiment, a single-use separation component is selected from the group consisting of a separation unit, a purification unit, a sterilizing filter and a combination thereof positioned along said length of tubing such that the biotechnology fluid can flow therethrough at a location upstream of said outlet end portion. In another embodiment, a disposable pressure sensor is positioned along the length of tubing such that the biotechnology fluid can flow therethrough at a location selected from the group consisting of upstream of the outlet end portion, downstream of the separation unit and upstream of the outlet end portion and a combination thereof.

It will be understood that the embodiments described above are illustrative of some of the applications of the principles of the present subject matter. Numerous modifications may be made by those skilled in the art without departing from the spirit and scope of the claimed subject matter, including those combinations or features that are individually disclosed or claimed herein. For these reasons, the scope hereof is not limited to the above description but is set forth in the following claims, and it is understood that the claims may be directed to the features hereof, including as combinations of features that are individually disclosed or claimed herein.

The invention claimed is:

1. A manifold system for biotechnology uses, comprising:
a manifold unit which is pre-sterilized and disposable so as to be adapted for single-time usage, including:
(a) at least one length of tubing having at least one inlet end portion, at least one outlet end portion, an outside surface, and an inside surface which is sterilized for passage of a biotechnology fluid therethrough,
(b) at least one single-use container in fluid communication with said tubing,
(c) at least one single-use sensor that senses parameter combinations that include a pH sensing function combined with at least one other sensing function selected from the group consisting of electrical conductivity, oxygen, temperature and combinations thereof,
(d) at least one valve remotely operable to engage the length of tubing;
(e) a single-use separation component selected from the group consisting of a separation unit, a purification unit, a sterilizing filter and a combination thereof positioned along said length of tubing such that the biotechnology fluid can flow therethrough at a location upstream of said outlet end portion;
a controller which controls operation of said valve, said controller having control logic which dictates the timing of opening and closing of said remotely operable valve responsive to the parameters sensed at the sensor;
the single-use sensor has usage counter capabilities, has an on-sensor memory device and an associated time event feature; and
the time event feature is initialized by achievement of a threshold event and is counted as sensor use after having been maintained for a pre-selected time interval, whereupon the counted sensor use is stored on and optionally retrievable from the memory device and accumulates with prior or subsequent uses, as needed until a maximum use total is attained.

2. The system in accordance with claim 1, wherein said control logic of the controller dictates the rate of flow of the biotechnology fluid imparted to the biotechnology fluid by a flow imparting unit.

3. The system in accordance with claim 2, wherein at least one said valve is a pinch valve.

4. The system in accordance with claim 1, further including a disposable pressure sensor positioned along said length of tubing such that the biotechnology fluid can flow therethrough at a location upstream of said outlet end portion, alternatively at a location downstream of said single-use separation component filter, when included, and upstream of said outlet end portion.

5. The system in accordance with claim 1, wherein said system is for tangential flow filtration, one said container is a process solution container, another said container is a permeate collection container, further including a disposable filter between said process solution container and said permeate collection container, whereby fluid from said process solution container is filtered through said single-use separation component and is collected in said permeate collection container, and a plurality of said valves at respective discrete locations along the tubing independently selectively allow or stop flow of the biotechnology fluid through said tubing at said discrete location for that valve.

6. The system in accordance with claim 5, wherein an inlet end is in operative communication with said process solution single-use container, and said tubing includes a recirculation length having at least one said valve between an exit port of said single-use separation component and said process solution single-use container.

7. The system in accordance with claim 6, further including a disposable pressure sensor positioned such that the biotechnology fluid can flow therethrough at a location between said single-use separation component and said valve along said recirculation length.

8. The system in accordance with claim 5, further including another single-use sensor downstream of said single-use separation component and optionally an additional single-use sensor upstream of said single-use separation component.

9. The system in accordance with claim 5, further including a disposable pressure sensor positioned such that the biotechnology fluid can flow therethrough at a location between said single-use separation component and a collection single-use container.

10. The system in accordance with claim 1, further including more than one said valve, and each valve independently selectively allows or stops flow of the biotechnology fluid through the length of tubing at each said location for that valve, wherein at least one of the valves controls passage of the biotechnology fluid within the system by operation of a flow imparting unit within or in operative engagement with the system.

11. The system in accordance with claim 1, wherein the single-use sensor monitors the combined parameters of pH, electrical conductivity and temperature or the combined parameters of pH, oxygen and temperature.

12. The system in accordance with claim 1, wherein said single-use sensor is a component of a disposable flow cell assembly that is configured to be releasably received and held by a non-disposable user interface at a docking location thereof.

13. The system in accordance with claim 12, wherein the disposable flow-through cell assembly includes a tube through which fluid to be monitored flows while being exposed to the single-use sensor.

14. The system in accordance with claim 1, wherein said single-use sensor is a component of a disposable bioreactor bag assembly that is configured to be releasably received and held by a non-disposable user interface at a docking location thereof that releasably receives and holds the disposable bag assembly.

15. The bioreactor system in accordance with claim 14, wherein the single-use sensor includes electrodes selected from the group consisting of at least two of a conductivity or oxygen working electrode, a conductivity or oxygen reference electrode, a pH working electrode, a pH reference electrode, a first external reference electrode, a second external reference electrode, a thermistor, and combinations thereof.

16. The system in accordance with claim 1, wherein said single-use sensor is a component of a disposable probe sensor assembly that includes an elongated probe having said single-use sensor and a connector configured to be releasably received and held by a non-disposable user interface at a docking location thereof.

17. The system in accordance with claim 1, further including input provisions to disable the sensor once the maximum use total is attained or to allow continued sensor use even after the maximum use total is attained.

18. The system in accordance with claim 1, wherein the single-use sensor includes electrodes selected from the group consisting of at least two of a conductivity or oxygen working electrode, a conductivity or oxygen reference electrode, a pH working electrode, a pH reference electrode, a first external reference electrode, a second external reference electrode, a thermistor, and combinations thereof.

19. A manifold system for biotechnology uses, comprising:
   a manifold unit which is pre-sterilized and disposable so as to be adapted for single-time usage, including:
   (a) at least one length of tubing having at least one inlet end portion, at least one outlet end portion, an outside surface, and an inside surface which is sterilized for passage of a biotechnology fluid therethrough,
   (b) at least one single-use container in fluid communication with said tubing,
   (c) at least one single-use sensor that senses parameter combinations that include a pH sensing function combined with at least one other sensing function selected from the group consisting of electrical conductivity, oxygen, temperature and combinations thereof,
   (d) at least one valve remotely operable to engage the length of tubing;
   (e) a single-use separation component selected from the group consisting of a separation unit, a purification unit, a sterilizing filter and a combination thereof positioned along said length of tubing such that the biotechnology fluid can flow therethrough at a location upstream of said outlet end portion;
   a controller which controls operation of said valve, said controller having control logic which dictates the timing of opening and closing of said remotely operable valve responsive to the parameters sensed at the sensor;
   the single-use sensor is for biopharmaceutical solution processing, has usage counter capabilities, an on-sensor memory device and an associated usage counter; and
   said usage counter utilizes motion detection to detect movement of a component of the system to thereby designate initializing of sensor usage and ceasing of motion detection to designate ceasing of sensor usage.

20. A manifold system for biotechnology uses, comprising:
   a manifold unit which is pre-sterilized and disposable so as to be adapted for single-time usage, including:
   (a) at least one length of tubing having at least one inlet end portion, at least one outlet end portion, an outside surface, and an inside surface which is sterilized for passage of a biotechnology fluid therethrough,
   (b) at least one single-use container in fluid communication with said tubing,
   (c) at least one single-use sensor that senses parameter combinations that include a pH sensing function combined with at least one other sensing function selected from the group consisting of electrical conductivity, oxygen, temperature and combinations thereof,
   (d) at least one valve remotely operable to engage the length of tubing;
   (e) a single-use separation component selected from the group consisting of a separation unit, a purification unit, a sterilizing filter and a combination thereof positioned along said length of tubing such that the biotechnology fluid can flow therethrough at a location upstream of said outlet end portion;
   a controller which controls operation of said valve, said controller having control logic which dictates the timing of opening and closing of said remotely operable valve responsive to the parameters sensed at the sensor;
   the single-use sensor has usage counter-capabilities, an on-sensor memory device and an associated time event feature;
   said time event feature is initialized by achievement of a threshold event and is counted as sensor use after having been maintained for a pre-selected time interval, whereupon the counted sensor use is stored on the memory device and accumulates with prior or subsequent uses, as needed until a maximum use total is attained;
   a usage counter utilizing motion detection to designate initializing of sensor usage and ceasing of motion detection to designate ceasing of sensor usage; and
   said time event feature and usage counter utilizing motion detection electronically interact to confirm total usage.

21. A manifold system for biotechnology uses, comprising:
   a manifold unit which is pre-sterilized and disposable so as to be adapted for single-time usage, including:
   (a) at least one length of tubing having at least one inlet end portion, at least one outlet end portion, an outside surface, and an inside surface which is sterilized for passage of a biotechnology fluid therethrough,
   (b) at least one single-use container in fluid communication with said tubing,
   (c) at least one single-use sensor that senses parameter combinations that include a pH sensing function combined with at least one other sensing function selected from the group consisting of electrical conductivity, oxygen, temperature and combinations thereof,
   (d) at least one valve remotely operable to engage the length of tubing;
   (e) a single-use separation component selected from the group consisting of a separation unit, a purification unit, a sterilizing filter and a combination thereof positioned along said length of tubing such that the biotechnology fluid can flow therethrough at a location upstream of said outlet end portion;
   a controller which controls operation of said valve, said controller having control logic which dictates the timing of opening and closing of said remotely operable valve responsive to the parameters sensed at the sensor;
   the single-use component is a biopharmaceutical solution processing device has gamma irradiation exposure reporting capabilities;
   an on-sensor memory device that maintains function under gamma irradiation;
   the on-sensor memory device has a stored pre-gamma irradiation threshold voltage and a stored post-gamma irradiation threshold voltage greater in magnitude than a pre-gamma threshold irradiation voltage; and
   the on-sensor memory device is readable, the pre-gamma irradiation threshold voltage correlates to a zero kGy gamma irradiation level, and the post-gamma irradiation threshold voltage correlates to a positive kGy gamma irradiation level substantially corresponding to a gamma irradiation exposure level for said sensor.

22. The sensor in accordance with claim 21, wherein the on-sensor memory device is a FRAM or an RFID device.

* * * * *